US00PP24070P3

(12) United States Plant Patent
Ruiz

(10) Patent No.: US PP24,070 P3
(45) Date of Patent: Dec. 10, 2013

(54) HYBRID TEA ROSE PLANT NAMED 'PC1251'

(50) Latin Name: *Rosa hybrida*
Varietal Denomination: PC1251

(75) Inventor: Juan Requena Ruiz, Córdoba (ES)

(73) Assignee: Plantas Continental, S.A., Posadas, Cordova (ES)

( * ) Notice: Subject to any disclaimer, the term of this patent is extended or adjusted under 35 U.S.C. 154(b) by 81 days.

(21) Appl. No.: 13/385,357

(22) Filed: Feb. 15, 2012

(65) Prior Publication Data

US 2013/0212752 P1 Aug. 15, 2013

(51) Int. Cl.
*A01H 5/00* (2006.01)

(52) U.S. Cl.
USPC ..... Plt./130

(58) Field of Classification Search
USPC ..... Plt./130
See application file for complete search history.

(56) References Cited

U.S. PATENT DOCUMENTS

PP21,247 P2 * 8/2010 Kordes ..... Plt./130

OTHER PUBLICATIONS

Pluto UPOV Citation for 'PC1251' Ecuador Published May 30, 2008.*

Pluto UPOV Citation for PC1251 CPVO Published Oct. 15, 2007.*

* cited by examiner

*Primary Examiner* — Wendy C Haas

(74) *Attorney, Agent, or Firm* — Jondle Plant Sciences Division of Swanson & Bratschun, L.L.C.

(57) ABSTRACT

A new variety of Hybrid Tea Rose named 'PC1251', particularly characterized by large, bicolor flowers with delicate fragrance, large dark red nearly thornless stems, and bright green foliage is disclosed.

4 Drawing Sheets

Genus and species: *Rosa hybrida.*
Variety denomination: 'PC1251'.

BACKGROUND OF THE NEW PLANT

The present invention comprises a new and distinct variety of Hybrid Tea Rose plant, botanically known as *Rosa hybrida*, and hereinafter referred to by the variety name 'PC1251'. 'PC1251' was discovered as a seedling resulting from a controlled cross in April of 2001 in Córdoba, Spain between the proprietary female Hybrid Tea Rose parent, '1200' (unpatented), and the proprietary male Hybrid Tea Rose parent, '5100' (unpatented). A single plant selection was subsequently chosen for further evaluation and for asexual propagation.

The new variety was first propagated via vegetative cuttings in Córdoba, Spain in 2001 and has been asexually reproduced repeatedly by vegetative cuttings for approximately two generations. 'PC1251' has been found to retain its distinctive characteristics through successive asexual propagations via vegetative cuttings.

Plant Breeder's Rights for this variety were applied for in the following countries: Europe on Jul. 23, 2007, Ecuador on May 29, 2007, and Colombia on Jun. 1, 2009. 'PC1251' has not been made publicly available or sold more than one year prior to the filing date of this application.

SUMMARY OF THE INVENTION

The following are the most outstanding and distinguishing characteristics of this new variety when grown under normal commercial practices in a greenhouse in Córdoba, Spain.

1. Large, bicolor flowers, with delicate fragrance;
2. Large, dark red, nearly thornless stems; and
3. Bright green foliage.

DESCRIPTION OF THE PHOTOGRAPH

This new Hybrid Tea Rose plant is illustrated by the accompanying photographs which show blooms, buds, and foliage of the plant. The colors shown are as true as can be reasonably obtained by conventional photographic procedures. The photograph is of a 2 year old plant taken in Córdoba, Spain and grown from rooted cuttings in a 24×24×24 centimeter pot in a greenhouse in Córdoba under conditions which approximate those generally used in horticultural practice.

Figure 1:
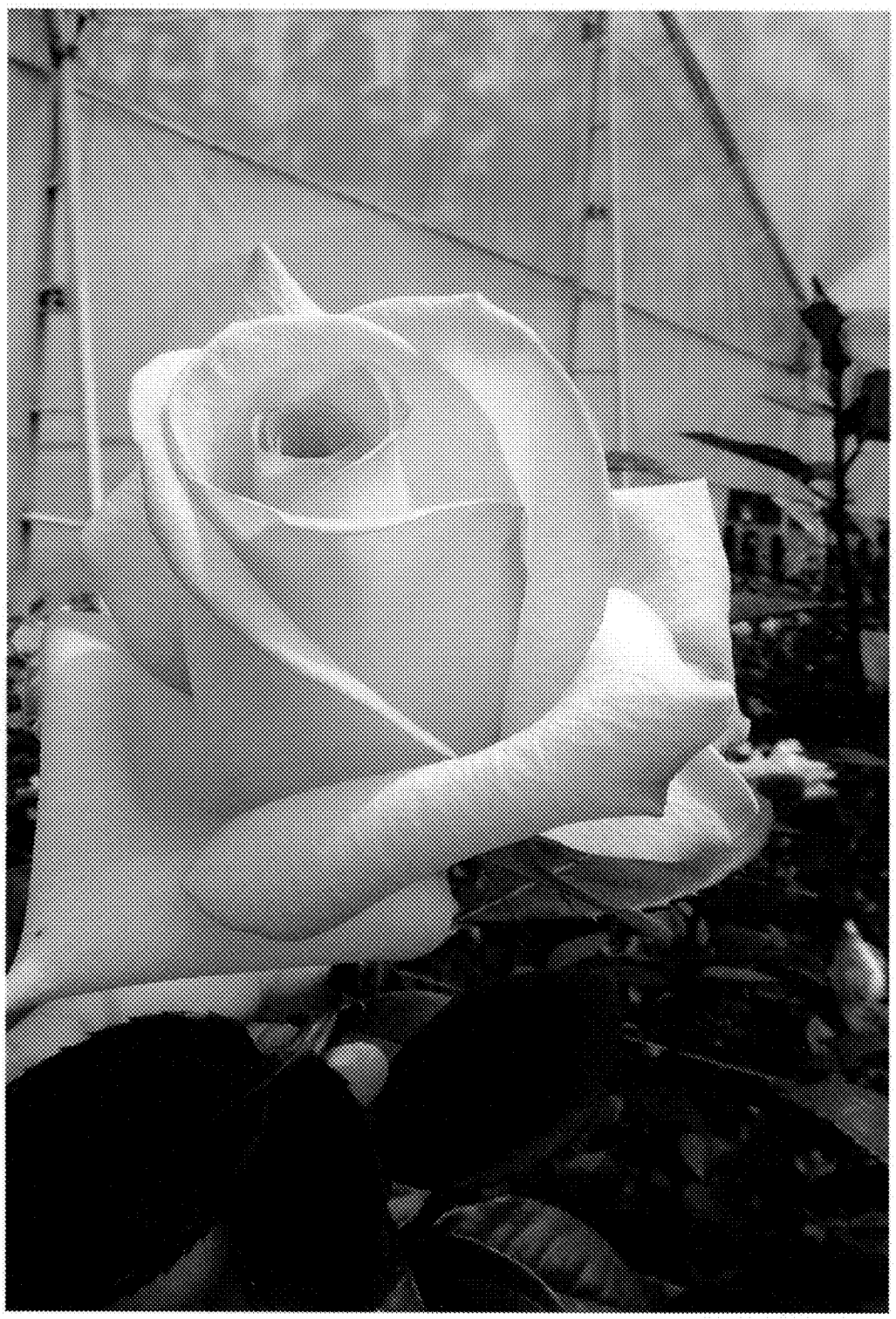
Figure 2:
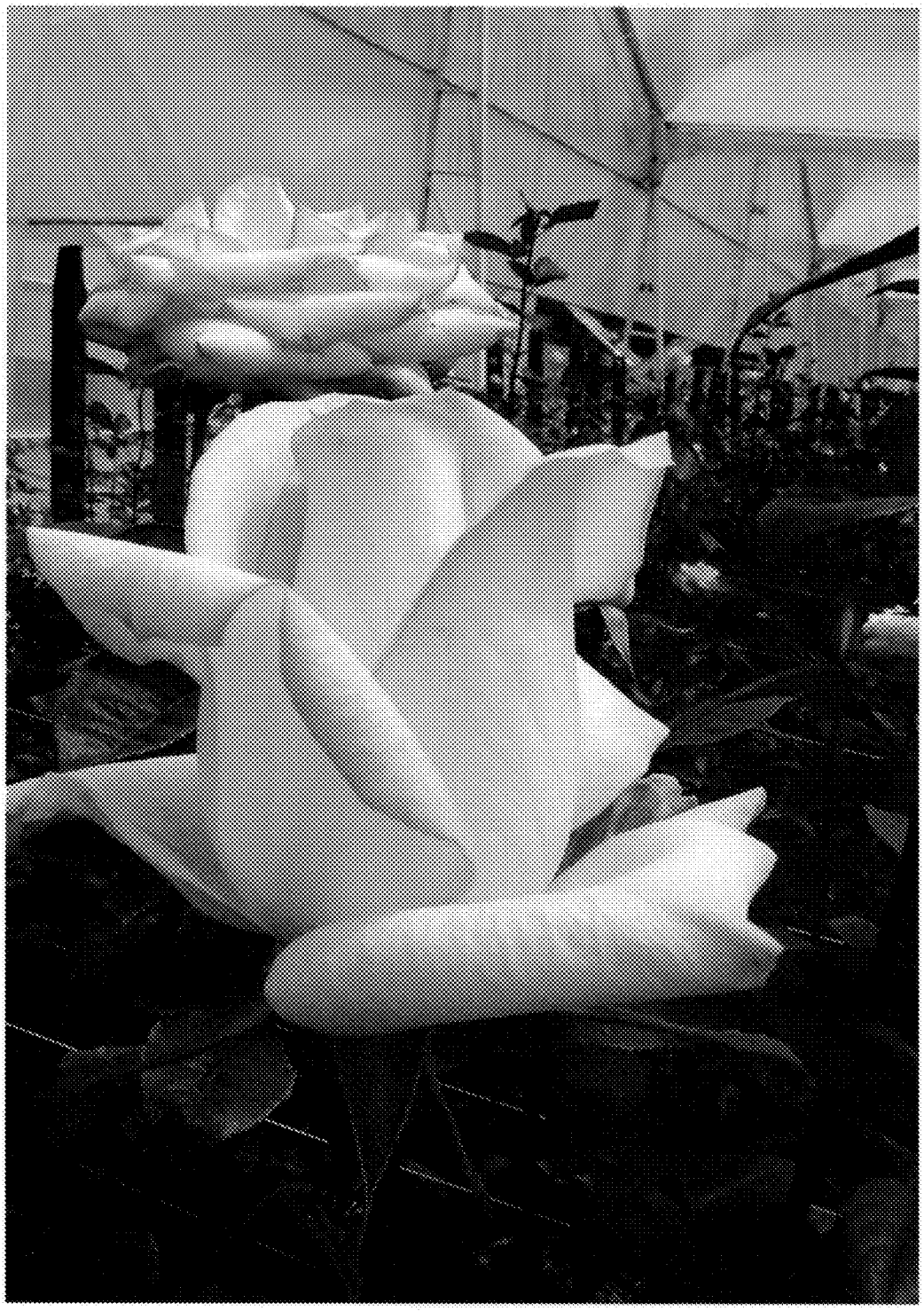
Figure 3:
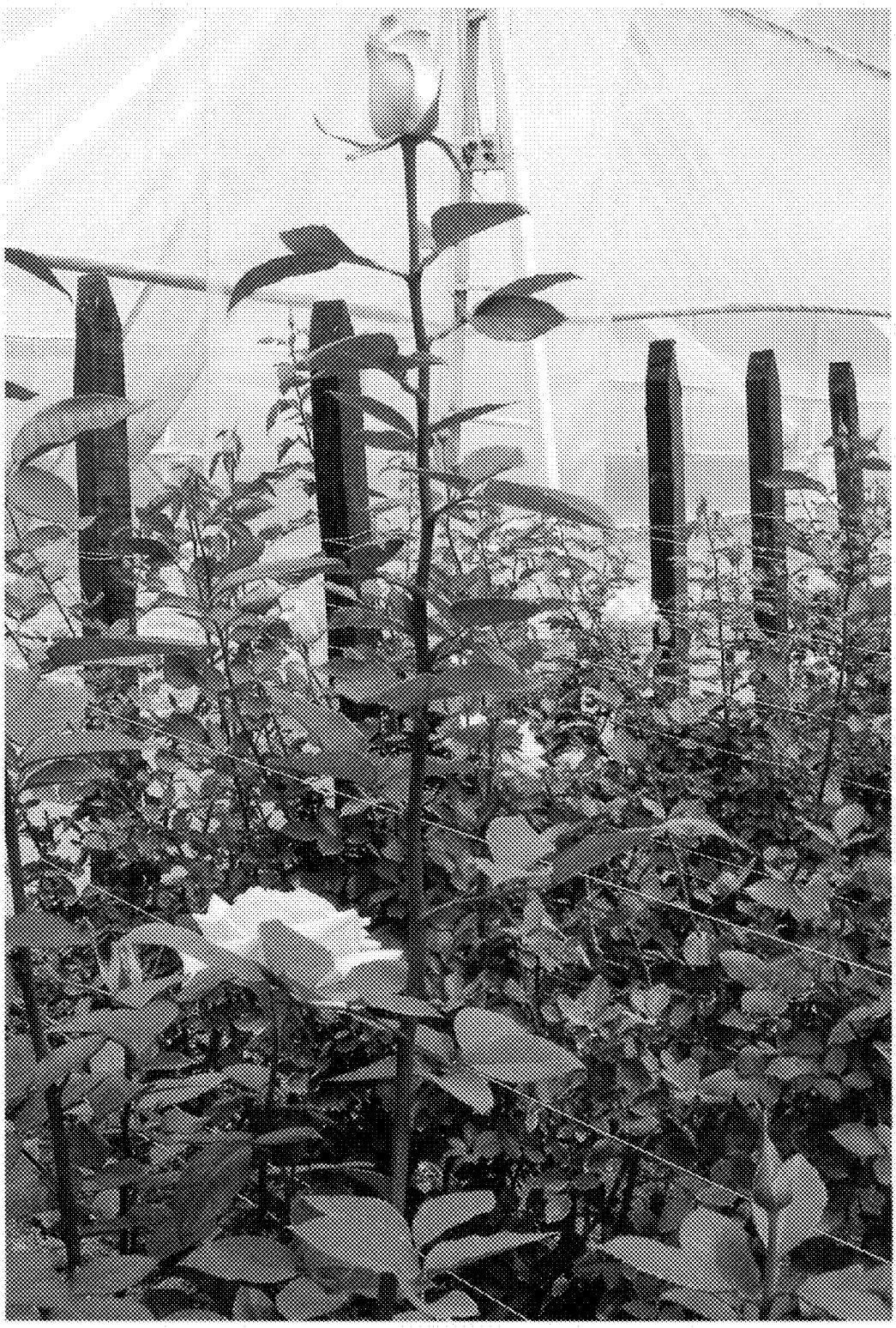
Figure 4:
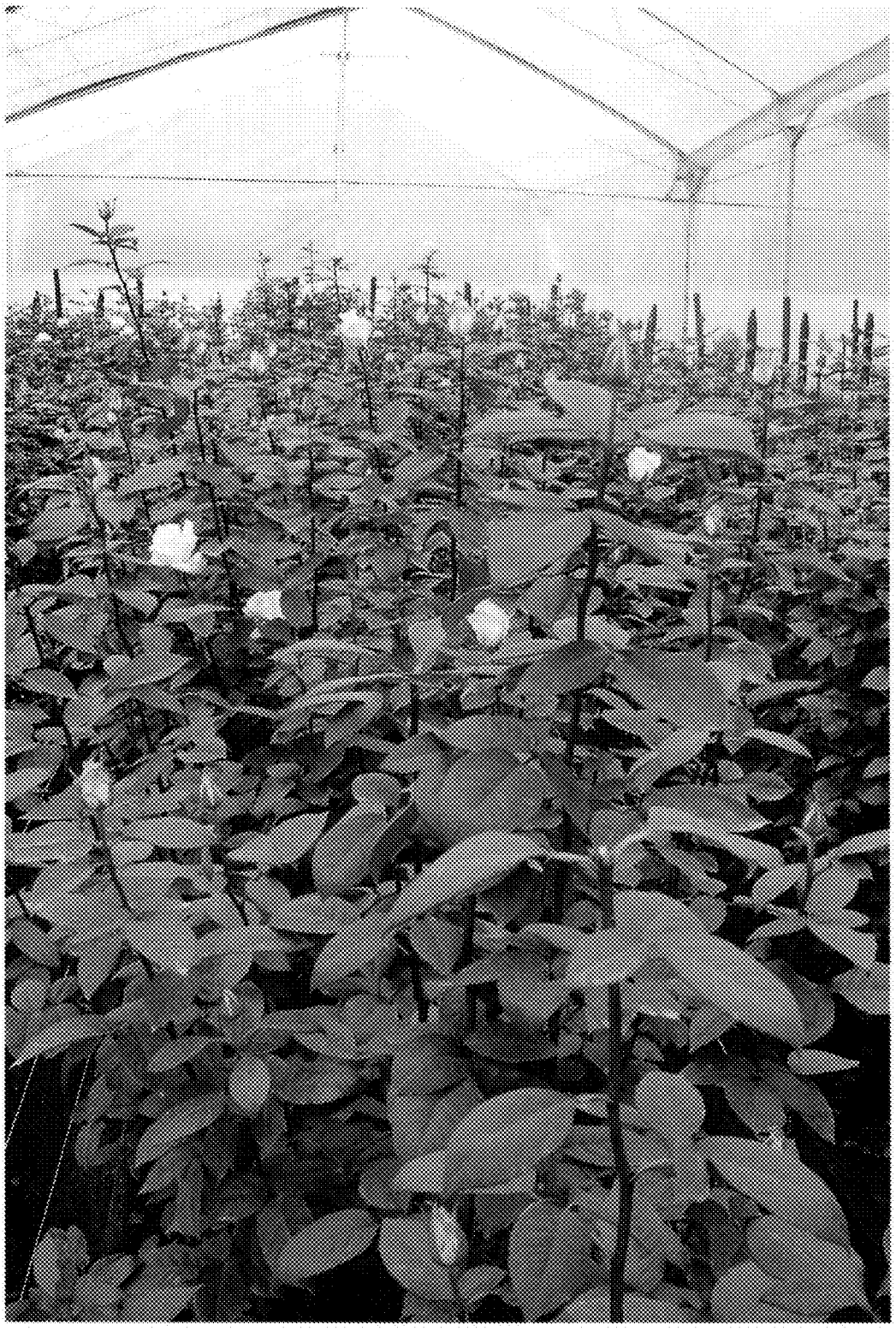

FIG. 1 shows a top view of a flower in full bloom.
FIG. 2 shows a side view of a flower in full bloom.
FIG. 3 shows an upright stem with a flower in mid bloom.
FIG. 4 shows overall plant habit with flowers in various stages of bloom.

DESCRIPTION OF THE NEW VARIETY

The following detailed descriptions set forth the distinctive characteristics of 'PC1251'. The data which define these characteristics were collected from asexual reproductions carried out in Córdoba, Spain. The plant history was taken on 2 year old plants grown in 24×24×24 centimeter pots in a greenhouse in Córdoba, Spain. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
*Family.*—Rosaceae.
*Species.*—*Rosa hybrida.*

*Common name*.—Hybrid Tea Rose.
*Denomination*.—'PC1251'.

Parentage:
*Female parent*.—The proprietary female Hybrid Tea Rose parent, '1200' (unpatented).
*Male parent*.—The proprietary male Hybrid Tea Rose parent, '5100' (unpatented).

Plant:
*Habit*.—Generally erect.
*Height*.—3.5 m.
*Spread*.—0.7 m.
*Life cycle*.—17 days.
*Form*.—Shrub.
*Time to produce a rooted cutting*.—60 days.
*Time to bloom from propagation*.—120 days.
*Lastingness of inflorescence on the plant*.—14 days.

Stems:
*Stem color*.—RHS 200A (Brown).
*Pubescence*.—Smooth.
*Stem form*.—Erect.
*Diameter*.—0.8 cm to 1.2 cm.
*Length*.—70.0 cm to 100.0 cm.
*Internode length*.—3.5 cm to 4.0 cm.

Leaves:
*Arrangement*.—1 leaflet.
*Shape*.—Ovate.
*Apex*.—Acute.
*Base*.—Rounded.
*Margin*.—Serrated.
*Surface texture* (*both upper and lower surfaces*).—Smooth.
*Length*.—9.0 cm.
*Width*.—5.0 cm.
*Color*.—Upper surface: RHS 147A (Dark green). Lower surface: RHS 147B (Light green).
*Surface pubescence*.—Smooth shiny.
*Petiole*.—Length: 2.0 cm to 2.5 cm. Color: RHS 139B (Yellow green).
*Venation color*.—RHS 143C.

Inflorescence:
*Umbels*.—None observed.
*Individual florets of the umbel*.—None observed.
*Fragrance*.—Weak fragrance.

Flower buds:
*Cluster shape*.—Single flower.
*Cluster size*.—Length: 6.0 cm to 7.0 cm. Width: 2.0 cm to 2.5 cm.
*Bud*.—Shape: Turbined. Apex: Acuminate. Base: Rounded. Color: RHS 143A (Green).

Petals:
*Quantity per flower*.—34.
*Shape*.—Rounded.
*Apex*.—Absent.
*Base*.—White.
*Margin*.—Smooth.
*Length*.—7.6 cm.
*Width*.—7.5 cm.
*Color*.—Outer side: RHS 155A (White) with RHS 54C (Dark pink) at edges. Inner side: RHS 155A (White).

Sepals:
*Number per flower*.—5.
*Shape*.—Elongated.
*Apex*.—Very acuminate.
*Base*.—Wide.
*Margin*.—Very broken.
*Color* (*upper surface*).—RHS 144A (Yellow green).
*Length*.—4.5 cm to 5.5 cm.
*Width*.—0.5 cm to 1.2 cm.

Peduncle:
*Length*.—8.0 cm.
*Diameter*.—0.4 cm to 0.8 cm.
*Color*.—RHS 187B (Grey purple).
*Texture*.—Smooth.

Reproductive organs:
*Stamens*.—Anther length: 0.3 cm to 0.4 cm. Filament length: 0.6 cm to 1.0 cm. Filament color: RHS 62C (Pink). Pollen amount: Abundant. Pollen color: RHS 14C (Yellow orange).
*Pistils*.—Number: 86. Stigma color: RHS 14A (Yellow orange). Style length: 1.1 cm. Style color: RHS 46B (Red).

Fruit and seed set: None observed.

Disease and insect resistance: No particular disease or insect resistance observed.

COMPARISON WITH PARENTAL VARIETIES

'PC1251'differs from the female parent, the proprietary female Hybrid Tea Rose plant '1200', in that 'PC1251' has bicolored flowers, while '1200' has white flowers. Additionally, 'PC1251'differs from the female parent '1200' in that 'PC1251' has large, reddish-colored stems that are 70 to 100 cm in diameter, while '1200' has medium sized, green-colored stems that are 40 to 60 cm in diameter. Further, 'PC1251' has bright green leaves with reddish-colored veins, while the leaves of '1200' are bright green throughout.

'PC1251' differs from the male parent, '5100', in that the flowers of 'PC1251' are white with dark pink edges, while the flowers of '5100' have two shades of pink bicolor. In addition, the flower size of 'PC1251' is larger than the flower size of '5100'. Further, 'PC1251' has bright green foliage, while '5100' has pale green foliage.

I claim:

1. A new and distinct variety of Hybrid Tea Rose plant named 'PC1251' as shown and described herein.

* * * * *